United States Patent
Smith

(12) 
(10) Patent No.: US 10,849,812 B2
(45) Date of Patent: Dec. 1, 2020

(54) METHOD AND APPARATUS FOR HEATED MASSAGE THERAPY

(71) Applicant: James F. Smith, Ontario, NY (US)

(72) Inventor: James F. Smith, Ontario, NY (US)

( * ) Notice: Subject to any disclaimer, the term of this patent is extended or adjusted under 35 U.S.C. 154(b) by 583 days.

(21) Appl. No.: 15/146,060

(22) Filed: May 4, 2016

(65) Prior Publication Data

US 2017/0319419 A1   Nov. 9, 2017

(51) Int. Cl.
*A61H 1/00* (2006.01)
*A61H 7/00* (2006.01)
*A61F 7/00* (2006.01)

(52) U.S. Cl.
CPC ............... *A61H 1/008* (2013.01); *A61F 7/00* (2013.01); *A61H 7/003* (2013.01); *A61F 2007/006* (2013.01); *A61F 2007/0035* (2013.01); *A61F 2007/0059* (2013.01); *A61F 2007/0087* (2013.01); *A61H 2201/0115* (2013.01); *A61H 2201/025* (2013.01); *A61H 2201/0207* (2013.01); *A61H 2201/0257* (2013.01); *A61H 2201/1695* (2013.01); *A61H 2203/02* (2013.01); *A61H 2205/06* (2013.01); *A61H 2205/065* (2013.01)

(58) Field of Classification Search
CPC ............... A61H 1/008; A61H 7/002; A61H 7/003–005; A61H 9/0021; A61H 9/0028; A61H 15/02; A61H 23/06; A61H 2201/0115; A61H 2201/025; A61H 2203/02; A61H 2205/06; A61H 2205/065; A61H 15/0092; A61H 39/04; A61H 39/06; A61H 2201/0207; A47K 7/02; A61F 7/00; A61F 2007/0035; A61F 2007/0059; A61F 2007/0087
See application file for complete search history.

(56) References Cited

U.S. PATENT DOCUMENTS

| | | | | |
|---|---|---|---|---|
| 1,965,861 A | * | 7/1934 | Schneider | A61H 7/003 606/131 |
| 2,638,527 A | * | 5/1953 | Curtis | A61F 7/007 601/15 |
| 3,878,837 A | * | 4/1975 | Werding | A61H 15/0085 601/148 |
| 4,432,355 A | * | 2/1984 | Delluc | A46B 13/06 15/29 |
| 4,722,326 A | * | 2/1988 | Ruderian | A61M 37/0092 401/2 |

(Continued)

FOREIGN PATENT DOCUMENTS

EP   0261481 A1   4/1987

OTHER PUBLICATIONS

Addaday Robert Froster Uno Roller; Fleet Feet Sports, https://www.fleetfeetsports.com/products/rf-uno; 2 pages.

(Continued)

*Primary Examiner* — Valerie L Woodward
(74) *Attorney, Agent, or Firm* — Duane C. Basch; Basch & Nickerson LLP

(57) ABSTRACT

A method and apparatus for the treatment of, and reduction of inflammation caused by, carpal tunnel syndrome. The apparatus employing a massage head made of a thermally conductive material attached to a handle. The apparatus is used to apply pressure, via the massage head, at or in proximity to the wrist through reciprocal movement.

7 Claims, 5 Drawing Sheets

(56) References Cited

U.S. PATENT DOCUMENTS

| | | | | |
|---|---|---|---|---|
| 4,787,373 | A * | 11/1988 | Vogel | A61F 7/007 |
| | | | | 601/15 |
| 5,374,226 | A * | 12/1994 | Grahm | A63B 23/16 |
| | | | | 482/44 |
| 5,792,081 | A * | 8/1998 | Cross | A61H 15/0092 |
| | | | | 601/123 |
| 5,817,037 | A * | 10/1998 | Zurbay | A61H 7/003 |
| | | | | 601/135 |
| 5,843,005 | A * | 12/1998 | Chubinsky | A61H 7/003 |
| | | | | 601/15 |
| 6,094,599 | A | 7/2000 | Bingham et al. | |
| 6,146,347 | A | 11/2000 | Porrata | |
| 6,254,555 | B1 * | 7/2001 | Sevier | A61H 7/001 |
| | | | | 601/134 |
| 6,953,440 | B2 | 10/2005 | Porrata et al. | |
| 6,979,305 | B2 | 12/2005 | Porrata et al. | |
| 7,476,207 | B2 | 1/2009 | Porrata et al. | |
| 7,481,783 | B1 * | 1/2009 | Kelley | A61H 15/0092 |
| | | | | 601/128 |
| 7,693,580 | B2 | 4/2010 | Docherty et al. | |
| 8,170,685 | B2 | 5/2012 | Docherty et al. | |
| 2003/0018286 | A1 | 1/2003 | Porrata et al. | |
| 2004/0049138 | A1 * | 3/2004 | Li | A61H 7/005 |
| | | | | 601/137 |
| 2005/0015032 | A1 * | 1/2005 | Stein | A61H 15/02 |
| | | | | 601/131 |
| 2008/0039753 | A1 | 2/2008 | Zomorodian et al. | |
| 2012/0253244 | A1 * | 10/2012 | Femano | A61H 7/004 |
| | | | | 601/84 |
| 2013/0273524 | A1 | 10/2013 | Ehrenkranz | |
| 2014/0276281 | A1 * | 9/2014 | Nefcy | A61H 7/003 |
| | | | | 601/138 |
| 2014/0277702 | A1 | 9/2014 | Shaw | |
| 2016/0166459 | A1 * | 6/2016 | Ghosh | A61H 7/001 |
| | | | | 601/137 |
| 2017/0172837 | A1 * | 6/2017 | Yang | A61H 7/005 |
| 2017/0258671 | A1 * | 9/2017 | Turner | A61H 7/008 |
| 2017/0273858 | A1 * | 9/2017 | Ngu | A61H 15/0092 |

OTHER PUBLICATIONS

Elasto-Gel Wrist Wrap; Active Forever Independent Living Products; https://www.activeforever.com/elasto-gel-wrist-wrap; 2 pages.
12 Home Remedies for treating Carpal Tunnel syndrome; Joint Essential; http://www.jointessential.com/12-home-remedies-for-treating-carpal-tunnel-sydrome/; 12 pages.
Carpal Tunnel Massage, Relieve Carpal Tunnel with Massage Therapy; Massage Envy; http://www.massageenvy.com/benefits-of-massage-therapy/carpal-tunnel-massage.aspx; 2 pages.
The Supplement Handbook: A Trusted Expert's Guide to What Works & What's Worthless for More than 100 Conditions, p. 126; Mark Moyad, MD, MPH; Rodale Books, 2014, 4 pages.
"How Common is Carpal Tunnel?," Penny Saver Publication-Webster-Penfield-Ontario, NY, edition; May 19, 2017; 2 pages.

* cited by examiner

METHOD AND APPARATUS FOR HEATED MASSAGE THERAPY

The disclosed method and apparatus are directed to the relief of nerve compression using a combination and pressure and head applied to the body, and more particularly to the relief of carpal tunnel syndrome in a person's wrist and hand.

BACKGROUND AND SUMMARY

Carpal Tunnel Syndrome (CTS) is a medical condition in which the median nerve is compressed as it travels through the wrist within the carpal tunnel and causes pain, numbness and tingling in the part of the hand that receives sensations from the median nerve. Inflammation is part of the complex biological response of body tissue to harmful stimuli, such as pathogens, damaged cells, or irritants. Inflammation is a protective measure that involves immune cells, blood vessels and molecular mediators. The purpose of inflammation is to eliminate the initial cause of cell injury, clean out neurotic cells and damaged tissues and to initiate tissue repair.

CTS is a nerve disorder in the hand that is caused by swollen, or inflamed tissue from repetitive and excessive motion that causes pressure on the median nerve within the carpal tunnel. CTS is the result of increased pressure on the nerve entering the hand from the forearm through the confined space of the carpal tunnel in the wrist. The bottom and sides of this channel are formed by the wrist bones and the top of the tunnel is covered by a strong band of connective tissue called a ligament. Symptoms of CTS include tingling, numbness, burning sensations and general discomfort in the wrist/hand area. Treatment has included rest, anti-inflammatory medications, steroid injections, surgery, and/or the use of wrist splints to restrain the wrist in either a neutral or extended position. While these measures may control symptoms temporarily, they have proven to be less successful in permanently controlling or relieving the effects of CTS.

Disclosed in embodiments herein is a pain management method for treating CTS, comprising: applying, at or in proximity to the wrist, a topical heat source, wherein the topical heat source is applied directly to the skin at or near the wrist to heat the subcutaneous region of the wrist and the carpal channel and the median nerve therein; and applying pressure, also at or in proximity to the wrist, using a thermally conductive material, in combination with the topical heat source, and reciprocally moving the thermally conductive material longitudinally along the wrist.

Further disclosed in embodiments herein is a handle suitable for grasping in a user's hand; and a massage head, operatively attached at one end of the handle, said massage head being formed of a thermally conductive material.

Figure 1:
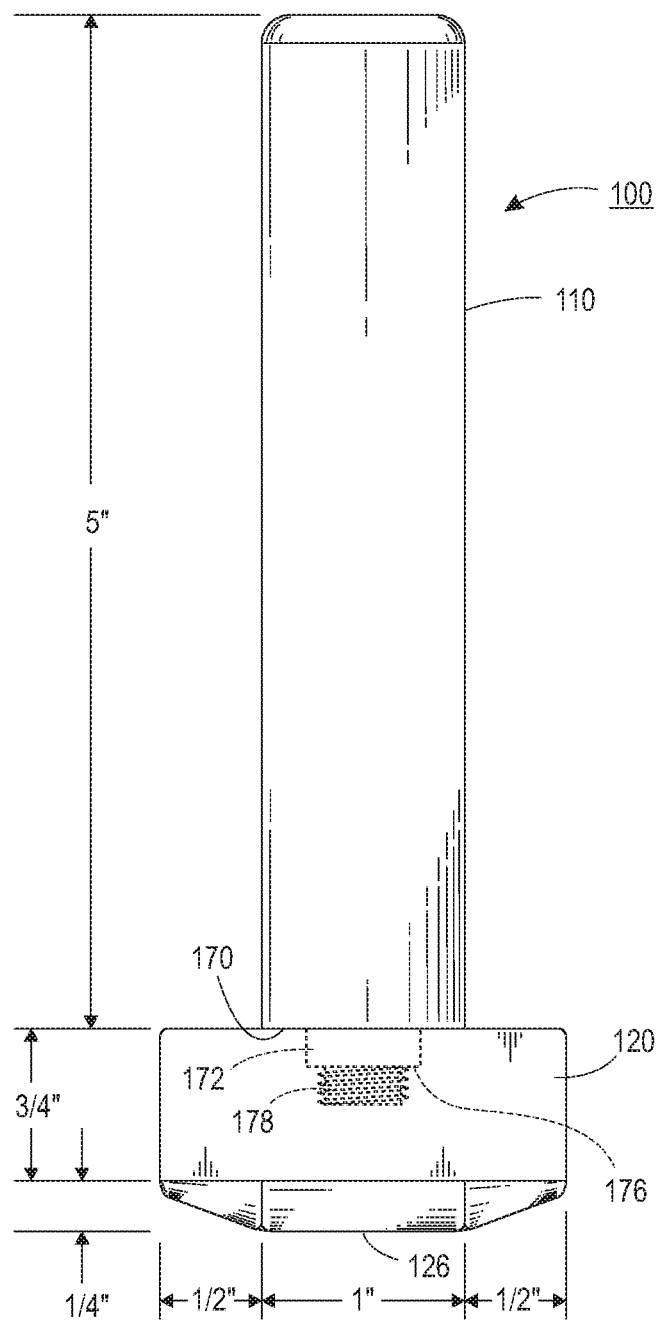
FIGS. 1-4 illustrate various views of an apparatus for use as a massage tool in accordance with aspects of the disclosed embodiments.

The various embodiments described herein are not intended to limit the disclosure to those embodiments described. On the contrary, the intent is to cover all alternatives, modifications, and equivalents as may be included within the spirit and scope of the various embodiments and equivalents set forth. For a general understanding, reference is made to the drawings. In the drawings, like references have been used throughout to designate identical or similar elements. It is also noted that the drawings may not have been drawn to scale and that certain regions may have been purposely drawn disproportionately so that the features and aspects could be properly depicted.

DETAILED DESCRIPTION

Figure 2:
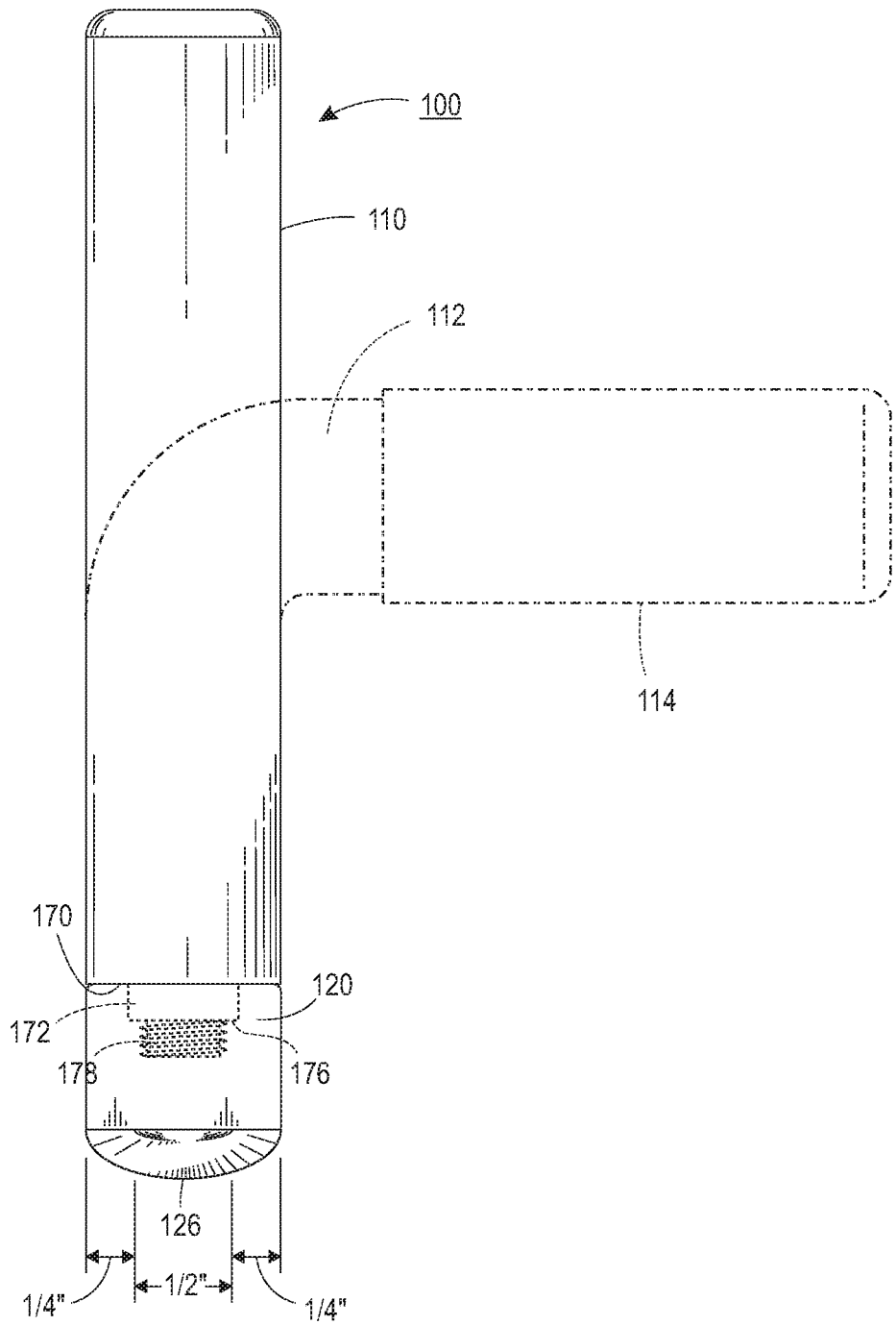
Figure 3:
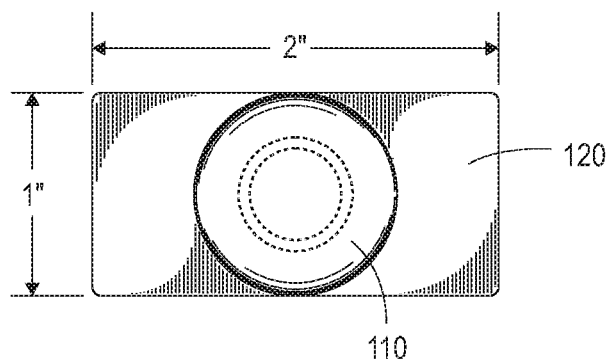

Referring initially to FIGS. 1-4, depicted therein are various views of an apparatus for use as a massage tool in accordance with aspects of the disclosed embodiments. In particular, apparatus 100 is suitable for applying a massaging pressure, particularly for treating carpal tunnel syndrome or other injuries and inflammation of minor joints in the hands and feet, for example. Apparatus 100 includes a handle 110 suitable for grasping in a user's hand, and the handle is attached to or formed with a massage head 120. As illustrated, head 120 is operatively attached at one end of the handle. In one embodiment the handle is attached to the head by mating threads as illustrated in FIGS. 1-2. For example, the handle may include shoulders 170 and 176, each leading to reduced diameter portions 172 and 178, respectively, which extend from the end of the handle. The last handle portion, 178, having a thread or similar mating structure on its surface to operatively, albeit removably, engage a corresponding interior surface within the head 120. In one embodiment, handle 110 is screwed and tightened into the corresponding recess of head 120 until the helical screw surfaces on portion 178 are engaged and the end or a shoulder of the handle bottoms out on a mating surface in the recess of the head 120. In order to remove the head 120 from handle 110, the respective pieces are simply turned in the opposite direction to disengage the helical screw surfaces.

In one embodiment, handle 110 is a straight handle consisting of a longitudinal member as illustrated in the view of FIG. 1. The handle may itself be made or formed from a thermally non-conductive material such as wood, plastic, compositions, etc. In an alternative embodiment, handle 110 may be made of a thermally conductive and dense material suitable for retaining heat in the same manner as the head, but further including an insulating optional sleeve or grip 114 applied over at least a portion of the handle so as to insulate a user's hand from the handle when it is being grasped.

Referring specifically to FIG. 2, an alternative configuration of the handle 110 is depicted, where instead of being a straight handle, it includes a curve or bend, and the unattached end used to grasp the handle extends at an angle. Although illustrated as a generally right-angle, it will be further appreciated that the handle may extend at various alternative angles that may make the apparatus more ergonomically suitable for a user to use one hand to grasp the apparatus and apply pressure to the wrist of the other hand. Furthermore, it is also contemplated that the angle or position of the alternative handle 112 relative to head 120 may be adjustable at various angles and positions. In yet another alternative embodiment, the orientation of the angled handle 112 relative to the massage head 120 may be changed or adjusted to facilitate easy grasping and orientation of the head relative to the wrist for massage.

Head 120 includes a lower contact surface that is smooth or non-abrasive so that it can easily slide over the skin. As illustrated, the head includes a recess for receiving a mating end of the handle 110. The head 120 may be formed of a thermally conductive material such as a dense clay or ceramic, bakelite, celluloid, crystallite, plastic, metal (e.g., stainless steel), and composites thereof, etc. In addition to being thermally conductive, the material may also be of a high density so that it retains heat to which it is exposed. As seen, for example, in FIG. 4, the bottom or contact surface 126 of head 120 may be further rounded and tapered so as to have no edges.

Figure 4:
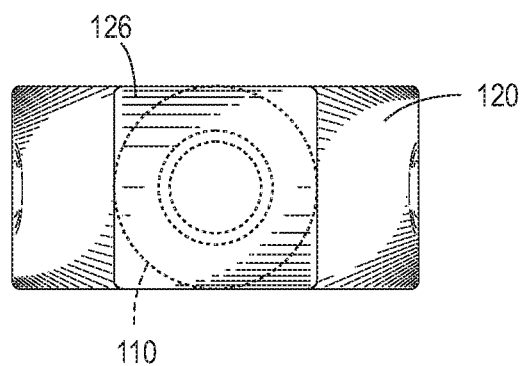
Figure 5:
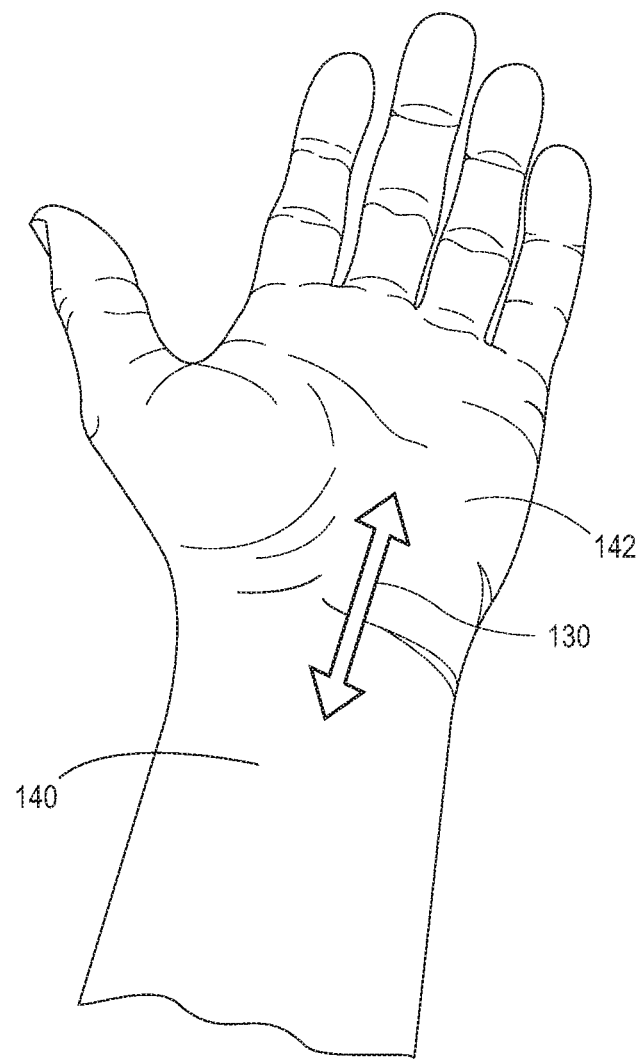
FIG. 5 is an illustration of the therapy method of massage in combination with the application of topical heat.

As illustrated, particularly in the side and bottom views of FIGS. 1 and 4, respectively, the massage head 120 includes a rounded outer surface for contact with the patient's body (e.g., wrist) while the handle is grasped and used to control the angle of the apparatus as well as to reciprocally move the massage head longitudinally along the wrist as illustrated in FIG. 5. More specifically, the massage head, while in contact with the skin and with moderate pressure being applied, is moved in the direction of arrows 130 over the region of the wrist 140 and lower palm 142. As will be appreciated, the massage head may be impervious to a topical heat source so that the heat source can be concurrently applied to the wrist while the massaging action is being performed.

Figure 6:
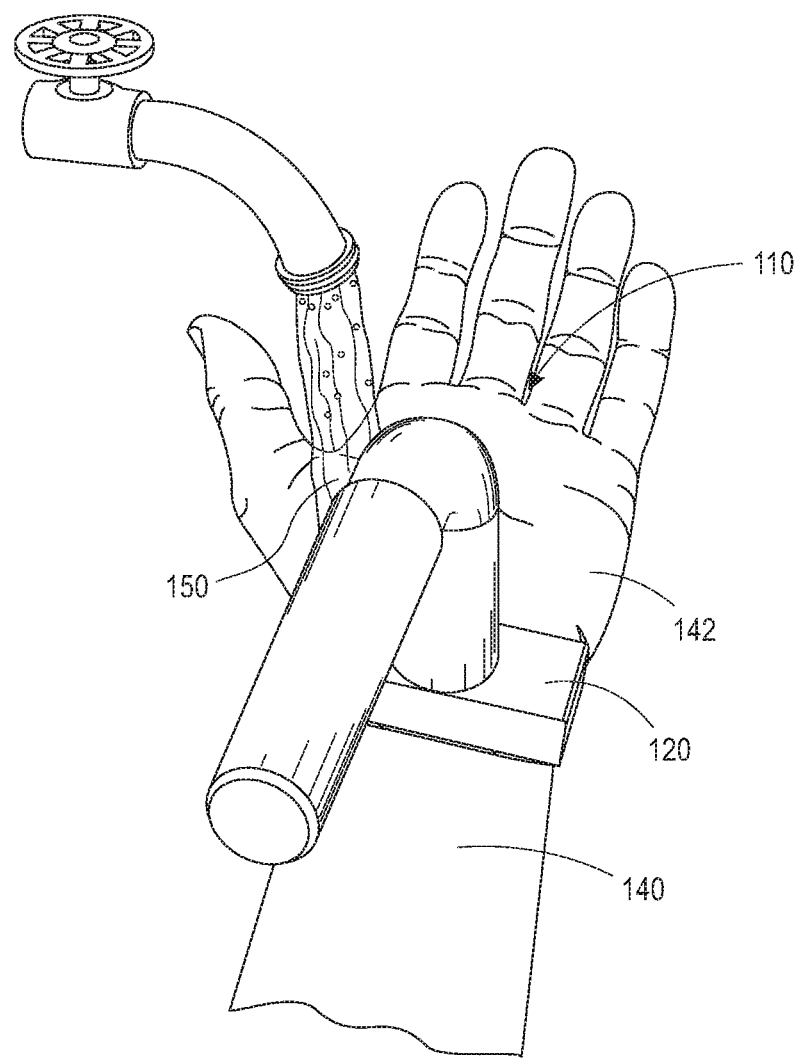
FIG. 6 is an illustration of an embodiment of a therapy method disclosed herein.

Having briefly described the apparatus depicted in FIGS. 1-4, attention is now directed to a therapy method as more specifically illustrated in FIGS. 5 and 6. In one embodiment, a pain management method for treating CTS includes applying or introducing, at or in proximity to a patient's wrist 140, a topical heat source 150, wherein the topical heat source is applied directly to the skin at or near the wrist and/or palm to heat the subcutaneous region of the wrist and the carpal channel (tunnel) and the median nerve therein. Next, and at the same time, pressure is applied, also at or in proximity to the wrist, using a thermally conductive material such as a massage head 120 of tool 110, in combination with continuing the topical heat source, and reciprocally moving the thermally conductive material longitudinally along the wrist.

In one method, the amount of pressure applied using the massage head 120 of tool 110 is about 9 psi, or within the range of 5-11.5 psi, or even 0-15 psi, and the pressure may be adjusted as a function of the patient's pain tolerance or tolerance of the therapy. Similarly, the temperature of the topical heat source is preferably at least about 110° F. but less than a scalding temperature, and likely less than about 120° F., and certainly less than about 130° F. As illustrated in FIG. 6, for example, the topical heat source introduced may be a fluid. While various fluids may be suitable, one embodiment contemplates the use of heated air as the heat source whereas another embodiment contemplates a topical heat source including a heated liquid. And, as suggested by FIG. 6, the heated liquid may include water as provided by a faucet or tap from a heated water source. Also, as noted above, the therapeutic massage using the head 120 of tool 110 is to be completed while the wrist and palm remain warmed from exposure to the topical heat source.

As an illustrative example, the following procedure may be performed:

(1) the tool 100, or at least massage head 110, may be preheated by immersing or coating the head for a period of time with the heated water or other topical heat source;

(2) the palm and wrist may be similarly pre-heated by application of the warm water so as to begin to warm the region where the wrist transitions to the palm—where the carpal tunnel is located;

(3) after preheating, the massage head is rubbed from a position on the wrist, through the end of the wrist and into the palm of the patient and then in a return direction, while maintaining a pressure on the handle so as to apply pressure to the patient's wrist and palm;

(4) by continuously and reciprocally massaging in the direction of arrow 130, inflammation is worked out of the patient's carpal tunnel in order to provide relief from pain commonly experienced with carpal tunnel syndrome.

It should be understood that various changes and modifications to the embodiments described herein will be apparent to those skilled in the art. Such changes and modifications can be made without departing from the spirit and scope of the present disclosure and without diminishing its intended advantages. It is therefore anticipated that all such changes and modifications be covered by the instant application.

What is claimed is:

1. A pain management method for treating carpal tunnel syndrome of a wrist, comprising:

introducing, at or in proximity to the wrist, a topical heat source in the form of a heated liquid, wherein the topical heat source is applied directly to skin at or near the wrist to heat the subcutaneous region of the wrist and the carpal channel and the median nerve therein; and at the same time applying uniform pressure across a surface of the wrist, using an elongated massage head in combination with the topical heat source, and reciprocally moving the massage head longitudinally along the wrist, said massage head, including a flat upper surface and a rounded lower contact surface along its length, being formed of a solid, thermally conductive material, and being directly attached at a center of the massage head to a handle suitable for grasping, whereby the handle is configured to be used to impart reciprocal movement to the massage head.

2. The method according to claim 1 wherein the amount of pressure applied is about 9 psi.

3. The method according to claim 1 wherein the temperature of the topical heat source is less than about 120° F.

4. The method according to claim 1 wherein the temperature of the topical heat source is less than about 130° F.

5. The method according to claim 1 where a contact surface of said massage head has an elongated shape.

6. The method according to claim 1 wherein the heated liquid includes water.

7. The method according to claim 1, wherein the reciprocal movement and pressure of the massage head is directed via the handle.

* * * * *